US006964202B2

(12) United States Patent
Buttle et al.

(10) Patent No.: US 6,964,202 B2
(45) Date of Patent: Nov. 15, 2005

(54) DETECTION OF ROLLING CONTACT FATIGUE

(75) Inventors: David John Buttle, Wantage (GB); Peter John Thayer, Oxford (GB); William Dalzell, Winchester (GB)

(73) Assignee: AEA Technology PLC, Didcot (GB)

( * ) Notice: Subject to any disclaimer, the term of this patent is extended or adjusted under 35 U.S.C. 154(b) by 0 days.

(21) Appl. No.: 10/243,678

(22) Filed: Sep. 16, 2002

(65) Prior Publication Data

US 2003/0070492 A1 Apr. 17, 2003

(30) Foreign Application Priority Data

Oct. 17, 2001 (GB) ............................................. 0124910

(51) Int. Cl.⁷ .......................................................... G01N 19/08
(52) U.S. Cl. ............................................................. 73/799
(58) Field of Search ........................ 73/761–799, 866.5

(56) References Cited

U.S. PATENT DOCUMENTS

| 3,358,225 | A |   | 12/1967 | Peugeot ....................... 324/40 |
|---|---|---|---|---|
| 3,742,357 | A |   | 6/1973 | Kubo ..................... 324/34 ST |
| 3,797,303 | A | * | 3/1974 | Bascoul et al. ............... 73/819 |
| 4,023,988 | A | * | 5/1977 | Stickels et al. ............. 148/622 |
| 4,408,294 | A | * | 10/1983 | Imam .......................... 73/593 |
| 4,462,257 | A | * | 7/1984 | Gerhart et al. ................ 73/644 |
| 4,522,071 | A | * | 6/1985 | Thompson .................... 73/597 |
| 4,661,777 | A |   | 4/1987 | Tornblom ................... 324/225 |
| 4,710,710 | A | * | 12/1987 | Flora et al. ................ 73/866.5 |
| 4,727,322 | A |   | 2/1988 | Lonchampt et al. ........ 324/229 |
| 4,770,046 | A | * | 9/1988 | Kanno et al. .................. 73/799 |
| 4,875,710 | A | * | 10/1989 | Mercado ....................... 285/24 |
| 4,926,692 | A | * | 5/1990 | Brokowski et al. ........... 73/597 |
| 5,394,084 | A |   | 2/1995 | Snyder ........................ 324/225 |
| 5,541,510 | A |   | 7/1996 | Danielson ................... 324/233 |
| 5,847,283 | A | * | 12/1998 | Finot et al. ................... 73/812 |
| 5,952,102 | A | * | 9/1999 | Cutler ........................ 428/408 |
| 6,353,656 | B1 | * | 3/2002 | LeVert et al. ................. 378/72 |
| 6,854,336 | B2 | * | 2/2005 | Buttle ......................... 73/779 |

FOREIGN PATENT DOCUMENTS

GB  2278450  11/1994  ............. G01L/1/12

OTHER PUBLICATIONS

Buttle et al.;"Probe Modelling to Enable Biaxial Stress Measurement Depth Profiling"; ISO Press 1995, pp. 41–52.*
David J. Buttle, William Dalzell, and Peter J Thayer; "Non–destructive Rapid Residual Stress Measurements in Rail Heads with Maps"; This paper was presented at a conference, in conference proceedings issued on Sep. 18, 2001.
D J Buttle, W Dalzell and P J Thayer; "Non–destructive Residual Stress Measurement in Rail Heads and Rolling Contact Fatigue"; INSIGHT, vol. 44,No. 6, Jun. 2002, pp 364–368.

* cited by examiner

Primary Examiner—Max Noori
Assistant Examiner—Alandra Ellington
(74) Attorney, Agent, or Firm—WillIam H. Holt

(57) ABSTRACT

The onset of rolling contact fatigue in an object may be detected by measuring the residual stresses in the surface of the object, and monitoring changes in their magnitude or their direction. The values of residual stresses in the surface are those averaged over a depth that may be in the range say 0.1 mm to 8.0 mm, for example about 2.5 mm. For ferromagnetic objects such as rails, the method may utilize an electromagnetic probe. Prior to rolling contact fatigue the surface stresses are compressive, and the onset of rolling contact fatigue may be characterized by a marked decrease of the stress in the generally transverse direction.

11 Claims, 5 Drawing Sheets

DETECTION OF ROLLING CONTACT FATIGUE

This invention relates to a method and apparatus for monitoring a material for the development of rolling contact fatigue; where the material is ferromagnetic the invention may use an electromagnetic probe.

BACKGROUND OF THE INVENTION

Where there is rolling contact between objects under a load, there may be the development of cracks. This may be a problem in bearings, and in the wheels or rails of railways. In the context of rails it has been found that such cracking, which may be referred to as head checking, may sometimes develop within a year of laying a new rail yet in other situations no such cracks develop over several decades. It would clearly be desirable to be able to monitor a material in situ to ascertain if rolling contact fatigue is developing, and particularly if the formation of cracks is incipient. Rolling contact fatigue may be presumed to arise from the stresses imposed on the material in use—by the passage of trains, in the case of a rail—but the exact mechanism for its development is not clear. The stresses in structures such as rails arise from various causes including changes of temperature, and the loads and pressures due to use. There may also be residual stresses arising from the fabrication of the structure or device, and any bending that the structure or device was subjected to during construction; the residual stresses arising from fabrication will also be affected by any stress-relieving heat treatment. As regards ferromagnetic materials, a variety of magnetic techniques are known to have some sensitivity to stress, although magnetic measurements are usually also affected by other material properties such as microstructure. A way of measuring stress in a steel plate is described in GB 2 278 450, this method using a probe containing an electromagnetic core to generate an alternating magnetic field in the plate, and then combining measurements from two sensors, one being a measure of stress-induced magnetic anisotropy, and the other being a measure of permeability. The probe is gradually turned around so the magnetic field has a plurality of different orientations in the plate, and these measurements are taken at each such orientation. The signals are affected not only by stress, but also by the lift off from the surface (i.e. the gap between the probe and the surface), and so must be corrected for lift off.

SUMMARY OF THE PRESENT INVENTION

According to the present invention there is provided a method for monitoring a rail of a railway line for the development of rolling contact fatigue, the method comprising measuring the residual biaxial stresses in the surface of the rail, and monitoring changes in their magnitude and/or their direction. A decrease of the compressive stress in the direction generally transverse to the longitudinal axis of the rail, or a change in the orientation of the principal stress axes of about 45°, would indicate the onset of rolling contact fatigue into a potentially hazardous state.

Surprisingly, although the mechanism for the development of rolling contact fatigue is not entirely clear, it has been found that the residual stresses in the surface change in a characteristic manner as rolling contact fatigue occurs. By monitoring these changes, the onset of rolling contact fatigue may be detected even before the formation of any cracks, or at any rate before the cracks are large enough to be detectable by any practicable means. Precautions or remedial action can therefore be taken, for example grinding off the surface layer, so that cracks never develop. Preferably the values of residual stresses in the surface are those averaged over a depth selected in the range say 0.1 mm to 8.0 mm, more preferably in the range 0.5 mm to 4.0 mm; the stresses at greater depths are of much less significance to the development of surface cracks, and do not appear to change significantly, while the stress at smaller depths such as 30 to 70 $\mu$m would be relieved by small surface proto-cracks (say 100–200 $\mu$m long) that are subsequently worn away by the passage of vehicles, and so that stress is not generally of relevance in the development of rolling contact fatigue.

Where the object is of ferromagnetic material, the method may utilise an electromagnetic probe.

Where the magnitude of the stresses is to be determined, the apparatus preferably comprises analysis means for resolving signals from the magnetic sensor into an in-phase component and a quadrature component (that is to say a component that is in phase with the drive current and with the generated alternating magnetic field, and a component in quadrature to that); means for mapping the in-phase and quadrature components directly into material property components and lift-off components; and means for deducing a value of the stress from the material property component so determined.

The mapping requires a preliminary calibration, with a specimen of the material, to determine how the in-phase and quadrature components of the signal vary with lift-off (at a constant stress) and vary with stress (at a constant lift-off), and deducing from the calibration measurements the applicable mapping for any stress and any lift-off. The mapping may be represented in the impedance plane (i.e. on a graph of quadrature component against in-phase component) as two sets of contours representing signal variation with lift-off (for different values of stress) and signal variation with stress (for different values of lift-off), the contours of both sets being curved. The contours of one set intersect the contours of the other set at non-orthogonal angles. Surprisingly it has been found that the angles at which the constant lift-off contours intersect any one contour of constant stress are all the same. Hence measurements taken along a few contours of each set enable the positions of the other contours of each set to be determined.

Surprisingly this simple mapping has been found to give an accurate representation of the variation of the signals with material property, in particular stress, and provides a simple way to distinguish these variations from variations arising from lift-off or other geometrical variations, which in the context of bearings, rollers, wheels or rails will typically arise as a result of curvature of the surface.

Preferably the electromagnet means comprises an electromagnetic core and two spaced apart electromagnetic poles, and the magnetic sensor is preferably arranged to sense the reluctance (or flux-linkage) of that part of the magnetic circuit between the poles of the electromagnet means. It is also desirable to arrange for such measurements to be taken with a plurality of different orientations of the magnetic field, at a single location on the object. This may be achieved using a single probe that is rotated at that location, measurements being taken with different orientations of the probe, or using an array of probes of different orientations that are successively moved to that location. In either case, the sensor or sensors provide a measure of the permeability of the material through which the flux passes between the poles, and so provide a signal indicative of the effective permeability of the material; the corresponding measurements at different probe orientations at a location on the object hence indicate the effective permeability in different directions.

The probe, or at least some of the probes, may also include a second magnetic sensor between the two poles and arranged to sense magnetic flux density perpendicular to the direction of the free space magnetic field between the poles. This second sensor would detect no signal if the material were exactly isotropic; however stress induces anisotropy into the magnetic properties of the material, and so the signals received by the second sensor (or flux-rotation sensor) are a measure of this stress-induced magnetic anisotropy. The variations in the flux rotation signals at different probe orientations, at a location on the object, enable the directions of the principal stress axes to be accurately determined. The flux rotation signals can also be related to the stress.

The probe, or at least some of the probes, may also include a third magnetic sensor (a flux-leakage sensor) between the poles and arranged to sense magnetic flux density parallel to the free space magnetic field. This third sensor will detect any flux leakage, this being influenced by changes in material properties, lift-off, and cracks. As with the flux-linkage sensor, measurements at a location are preferably made at different probe orientations.

The reluctance (or flux-linkage) signal from the or each probe is preferably backed-off, i.e. processed by first subtracting a signal equal to the signal from that sensor with the probe adjacent to a stress-free location. The backed-off signal is then amplified so the small changes due to stress are easier to detect. This backing off is performed after resolving into in-phase and quadrature components but before performing the mapping. Preferably the signals from the or each probe are digitized initially, and the backing-off and resolution are performed by analysis of the digital signals.

To achieve penetration below the surface of the ferromagnetic object it is desirable to operate at alternating frequencies less than 200 Hz, for example between 5 Hz and 100 Hz (which in mild steel provide penetrations of about 5 mm and 1 mm respectively). In other situations, where such depth of penetration is not required, higher frequencies can be used, for example up to 150 kHz for a penetration of only about 15 $\mu$m.

Generally, the more different probe orientations are used for taking measurements the more accurate the determination of stress levels and principal axes can be, and so the sensitivity to the onset of rolling contact fatigue will be enhanced. The directions of the principal axes may be ascertained from flux-linkage, flux-leakage, or flux rotation signals: the signal maxima and minima for flux-linkage and flux-leakage would be expected to be along these directions, whereas those for flux-rotation would be along the bisection angles between these directions. If the surface is curved, the flux-rotation signal response will however be modified by the curvature.

BRIEF DESCRIPTION OF THE DRAWINGS

The invention will now be further and more particularly described, by way of example only, and with reference to the accompanying drawings, in which.

DETAILED DESCRIPTION OF THE INVENTION

Figure 1:
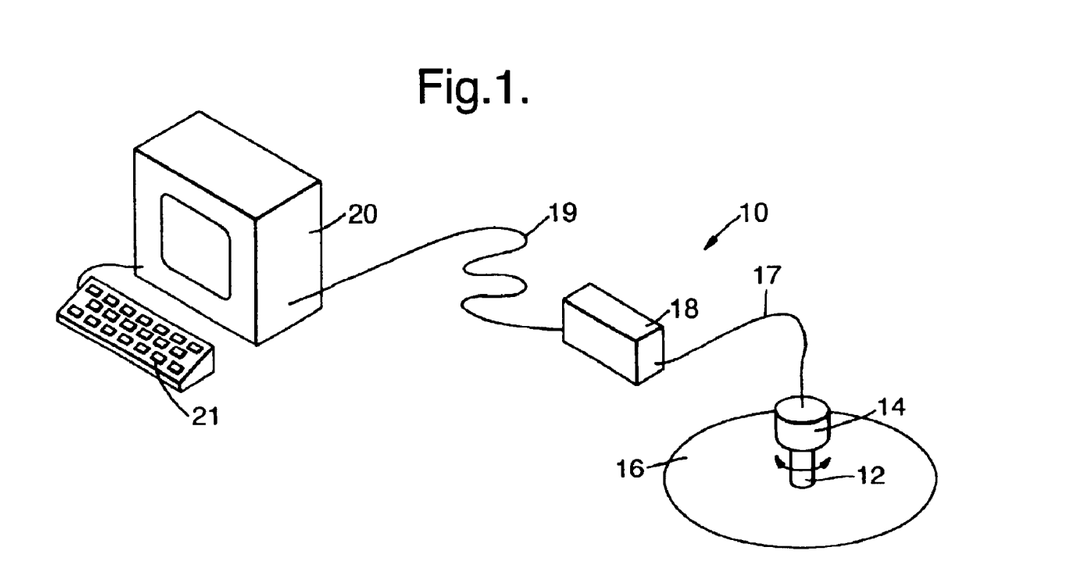
FIG. 1 shows a diagrammatic view of an apparatus for measuring stress.

The invention will be described with reference to an apparatus suitable for measuring the stresses in a ferromagnetic object, such as a rail. Referring to FIG. 1, a stress measuring apparatus 10 includes a sensor probe 12 comprising sensors for flux-linkage, flux-rotation and flux-leakage, the probe 12 being attached to an electric motor 14 which can be held by an operator, so the motor 14 can turn the probe 12 with one end adjacent to a surface of a steel object 16 in which the stress is to be determined. The sensor probe 12 and motor 14 are connected by a 2 m long umbilical cable 17 to a signal conditioning/probe driver unit 18. The unit 18 is connected by a long umbilical cable 19 (which may for example be up to 300 m long) to an interface unit within a microcomputer 20, which has a keyboard 21. Operation of the apparatus 10 is controlled by software in the microcomputer 20.

The interface unit within the microcomputer 20 generates sine and cosine functions at an angular frequency selectable by software, and buffers the sine waveform for transmission to the unit 18 for driving the probe 12. The amplitude of the transmitted waveform is also selectable by software. It also provides signals to control the motor 14 and hence the angular position of the probe 12. The interface unit also provides control signals to the unit 18 to select which of the signals available from the probe 12 is to be transmitted for analysis. It demodulates the selected input to derive its in-phase and quadrature components, filters the demodulated signal to remove high frequency components and to reduce noise, and converts the analogue signals to digital form for input to the computer 20. It also detects the angular position of the probe 12 from signals provided by a position encoder (not shown) on the motor 14.

The long umbilical cable 19 incorporates a coaxial cable to transmit the selected signal, and wires to control which signal is selected, to control the motor 14, to transmit signals from the position encoder, to transmit the sinusoidal waveform, and to convey electrical power. The unit 18 converts the drive waveform from a voltage to a current drive for the probe 12; buffers and amplifies the signals from the probe 12; and selects which signal is to be transmitted to the microcomputer 20. It also buffers the signals from the position encoder for transmission, and drives the motor 14 in response to control signals.

Figure 2:
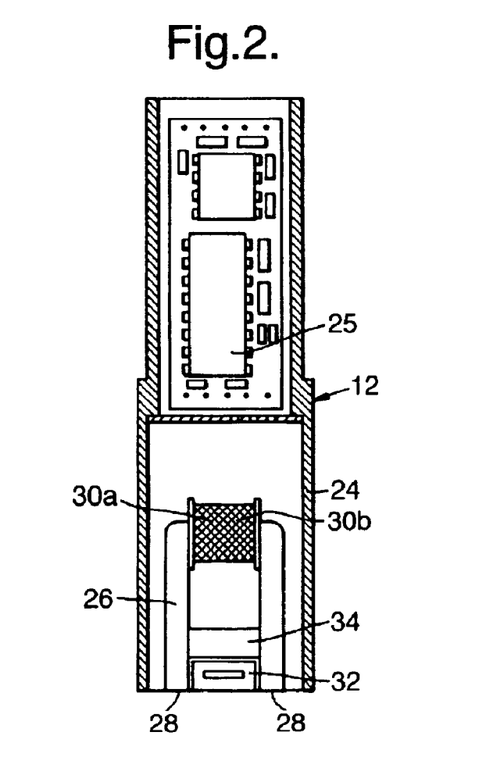
FIG. 2 shows a longitudinal sectional view of a probe for use in the apparatus of FIG. 1.

Referring now to FIG. 2, the probe 12 is shown detached from the motor 14, in longitudinal section although with the internal components shown in elevation (the connecting wires within the probe 12 are not shown). The probe 12 comprises a cylindrical brass casing 24 of external diameter 16.5 mm and of overall height 60 mm, the upper half being of reduced diameter whereby the probe 12 is attached to the motor 14. The upper half of the casing 24 encloses a head amplifier 25. The lower half encloses a U-core 26 of laminated mu-metal (a high permeability nickel/iron/copper alloy) whose poles 28 are separated by a gap 7.5 mm wide, and are each of width 2.5 mm, and of thickness 10 mm (out of the plane of the figure.) The poles 28 are in the plane of the lower end of the casing 24, which is open. Around the upper end of the U-core 26 is a former on which are wound two superimposed coils 30. One coil 30a (which has 200 turns) is supplied with the sinusoidal drive current from the unit 18; the other coil 30b (which has 70 turns) provides flux-linkage signals.

Between the two poles 28 is a former on which is wound a 1670-turn rectangular coil 32, about 4 mm high and 6 mm wide, and 6 mm-square as seen from below, the windings lying parallel to the plane of the figure so the longitudinal axis of the coil 32 is perpendicular to the line between the centres of the poles 28. The coil 32 is supported by a support plate 34 fixed between the arms of the U-core 26 so the lower face of the coil 32 is in the plane of the poles 28. The coil 32 provides the flux-rotation signals. On the same former as the foil 32 is wound a 200-turn rectangular coil, the windings being perpendicular to the plane of the figure so the axis of the coil is parallel to the line between the centres of the poles 28. This coil provides flux leakage signals. All three signals are amplified by the head amplifier 25 before transmission to the unit 18.

In operation of the system 10, the motor 14 is supported so the lower end of the probe 12 is adjacent to the surface of the object 16 and the longitudinal axis of the probe 12 is normal to the surface. An alternating current of the desired frequency and amplitude is supplied to the drive coil 30a, so the magnetic field in the object 16 oscillates about zero with an amplitude much less than saturation. The probe 12 is first placed adjacent to a region of the object 12 where the stresses are negligible. The in-phase and quadrature components of the flux linkage signal received by the microcomputer 20 are each backed off to zero, and the backing off values are then fixed. During all subsequent measurements the flux linkage components are backed off by these same amounts (i.e. subtracting a signal equal to the component observed when in a stress-free location).

Measurements can be taken by placing the probe 12 adjacent to a region where the stress is to be measured. The orientation of the line joining the centres of the poles 28 (referred to as the orientation of the probe 12) is noted relative to a fixed direction on the surface. The motor 14 is then energized to rotate the probe 12, for example in a step-wise fashion 10° at a time through a total angle of 360°. At each orientation of the probe 12 all the signals are measured. These measurements may be made at different frequencies, for example with a drive current frequency of 68 Hz when measuring flux rotation and at a frequency of 300 Hz when measuring flux linkage, but more typically the drive current frequency would be the same when measuring signals from all the sensors.

It will be appreciated that the invention is applicable with many different probes. The probe 12 might for example be modified by using a U-core 26 of a different material such as silicon iron (which can provide higher magnetic fields), or indeed the drive coil might be air-cored. The probe might be of a different shape or size, for example for inspecting surface stress in a small bearing it may be appropriate to use a probe of diameter as small as 3 mm, and to operate at a higher frequency such as 100 kHz, while for inspecting internal stresses in a large steel girder it may be appropriate to use a probe of diameter say 75 mm.

The flux rotation signals vary sinusoidally with probe orientation, so the orientation at which they have their maxima and minima can be determined. The directions midway between these two orientations are the directions of the principal stress axes. Measurements of flux rotation are therefore useful if the principal stress directions are unknown. The flux linkage and flux leakage signals also vary sinusoidally with probe orientation (in antiphase with each other) and the values are observed at the principal stress directions. If the principal stress directions are already known, then the probe 12 might instead be merely oriented to those directions, and flux linkage and flux leakage measurements made; no rotation of the probe 12 would be necessary.

Figure 3:
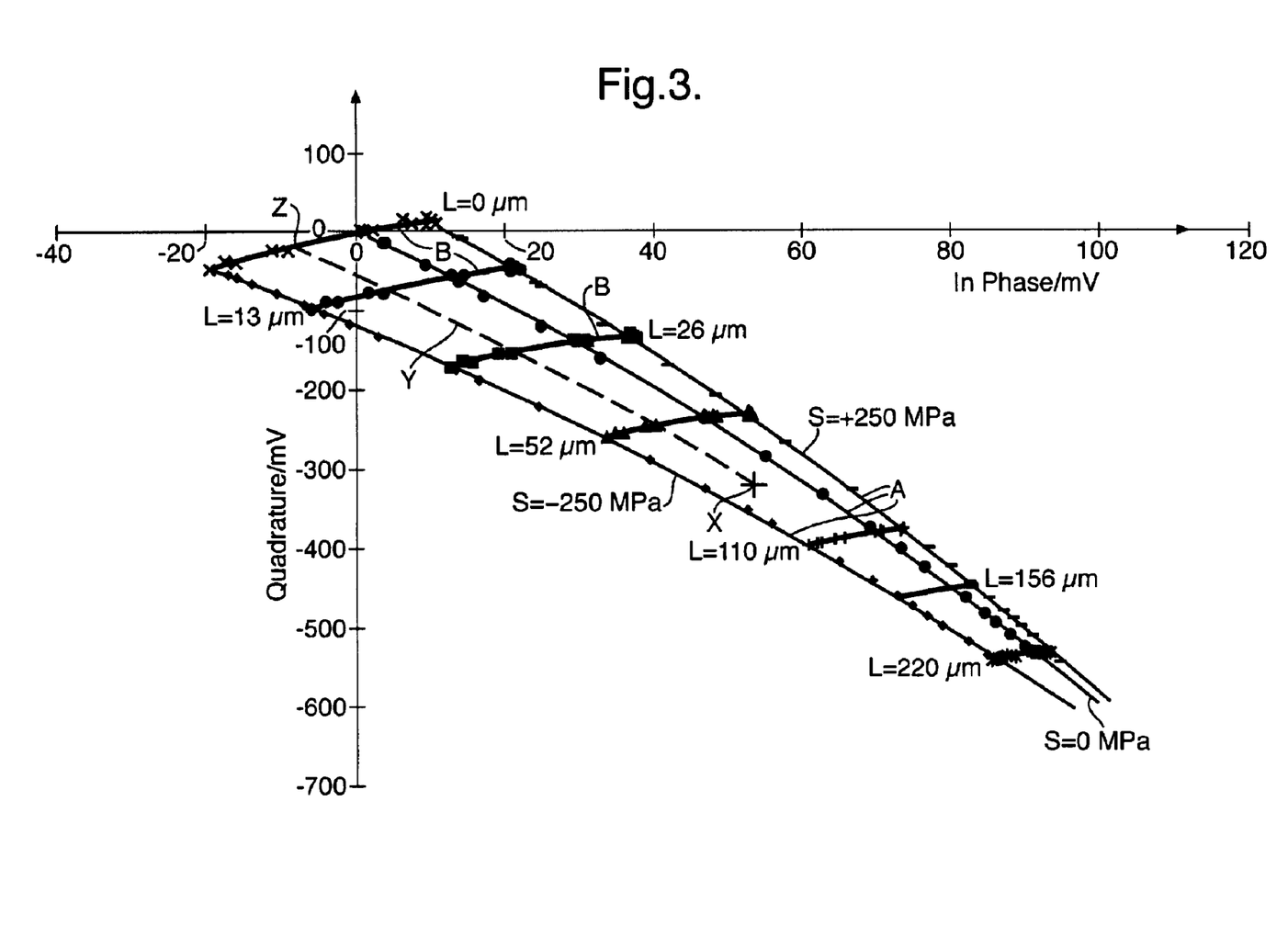
FIG. 3 shows graphically the variation of the backed-off quadrature and in-phase components of flux-linkage with variations of lift-off, and with variations of stress.

The values of the stresses in the directions of the principal stress axes can be determined from the experimental measurements of flux linkage with the probe 12 oriented in those directions. This requires calibration of the apparatus 10, taking measurements on a sample of material of the same type as that of the object 16, while subjecting it to a variety of different stresses. This may be done with a rectangular strip sample in a test rig, flux linkage measurements being made at the centre of the sample where the principal stress direction is aligned with the axis of the test rig. Referring to FIG. 3 this shows the backed-off flux linkage in-phase and quadrature components obtained in such a test rig, the measurements being made with a drive frequency of 70 Hz, and the specimen being a steel bar. A first set of measurements were made at progressively larger values of lift-off, L, but with no stress, S. This gives the lift-off contour A, the lift-off varying between 0 and 220 $\mu$m. Similar lift-off contours A are obtained for other fixed values of stress, those for S=250 MPa tension and compression being shown. Measurements were then made at a range of different fixed values of lift-off, L, with varying stresses, S (both compression and tension), providing the contours B.

It will be appreciated that the contours A are curved, and the contours B are not orthogonal to the contours A, but that they intersect at a substantially constant angles along any one lift-off contour A. Consequently it is only necessary to make calibration measurements sufficient to plot a few such contours A and B, and the shapes of the other contours can be predicted. It has also been found that this intersection angle, and the curvature of the contours, are characteristic of the material.

After calibrating the probe 12 in this manner, measurements of stress can be readily made from observations of flux linkage signals (resolved and backed off), as the contours enable the changes due to lift-off to be readily distinguished from changes due to stress. Any particular position in the impedance plane (i.e. in the graph of quadrature against in-phase components) corresponds to a particular value of stress and a particular value of lift-off. The mapping between (in-phase, quadrature) coordinates and (stress, lift-off) coordinates may be carried out graphically, referring to such contours, or by calculation. For example if the signal has the in-phase and quadrature components of the position marked X, this corresponds to a lift-off of about 80 $\mu$m and a stress of about 125 MPa. Alternatively this value X may be translated (along the broken line Y) along a contour A of constant stress to find the in-phase and quadrature components at position Z for zero lift-off.

The value of stress found in this way is, it will be appreciated, the uniaxial stress that would provide that value of the flux linkage signal. If the stresses are actually biaxial, then a further calibration must be carried out with a cross-shaped sample in a test rig, flux linkage measurements being made at the centre of the sample where the principal stress directions are aligned with the axes of the test rig. Hence a graph or map may be obtained for a range of values of stress on one axis (say the x-axis) and for a range of values of stress on the other axis (say the y-axis), with contours each of which shows the values of biaxial stress that give a particular value of apparent uniaxial stress along the x-axis; and a similar graph may be obtained with contours showing values of biaxial stress that give a particular value of apparent uniaxial stress along the y-axis. Hence from measurements of apparent uniaxial stress along the two principal stress axes obtained as described earlier, the biaxial stress can be determined.

It will again be appreciated that the biaxial stress may be determined either graphically or by calculation in this way. Apparent values of uniaxial stress (in MPa) may be used for this purpose, or alternatively the numerical value of the flux-linkage signal (in mV), either the in-phase or quadrature value, obtained by eliminating the effect of lift-off as described in relation to FIG. 3, may be used.

The same signal analysis can be performed using the in-phase and quadrature components of the flux leakage signal, so it too can be corrected for lift-off. This signal is influenced by material properties and also by cracks. If corrected for lift-off, and also normalised for stress, it can be used to detect cracks. Stress normalisation may be achieved by calculating the ratio between the amplitudes of the sinusoidal variations with direction of the flux leakage and the flux linkage signals. This ratio may be used as a cracking parameter.

Within a railway line as initially laid there are residual stresses arising from the manufacturing process, and these are typically tensile in the head and the foot of the rail but compressive in the web. Trains passing over the line cause the surface layers of the railhead to undergo plastic deformation, and the resulting stress field is compressive near the surface. In a compressive stress environment crack initiation is inhibited, so this state of compression near the surface is desirable. (Indeed, in the manufacture of bearings, the manufacturing process aims to establish such a compressive layer initially.)

Measurements of residual stresses averaged within about 2 mm of the surface in the railhead have shown the following trends associated with the onset of rolling contact fatigue.

1. The compressive stresses are initially isotropic (equi-biaxial), but they gradually become more anisotropic, with the compressive stress axis of larger magnitude being in a generally longitudinal direction (although this direction may be at an angle in the range 10° to 35° to the longitudinal axis of the rail).

2. The compressive stress component in the generally transverse direction decreases.

3. The stress component in the generally transverse direction becomes tensile, and the orientation of the principal stress axes tends to rotate through about 45°.

4. As surface cracks develop, the stress component in the longitudinal direction also becomes tensile.

It will be appreciated that the changes in stage 1 are not a cause for concern, but that detection of the decrease of stage 2 is a sign that rolling contact fatigue is imminent; detection of the characteristics of stage 3 in a rail would suggest that small cracks may have already started; and the characteristics of stage 4 shows that cracks exist.

Figure 4A:
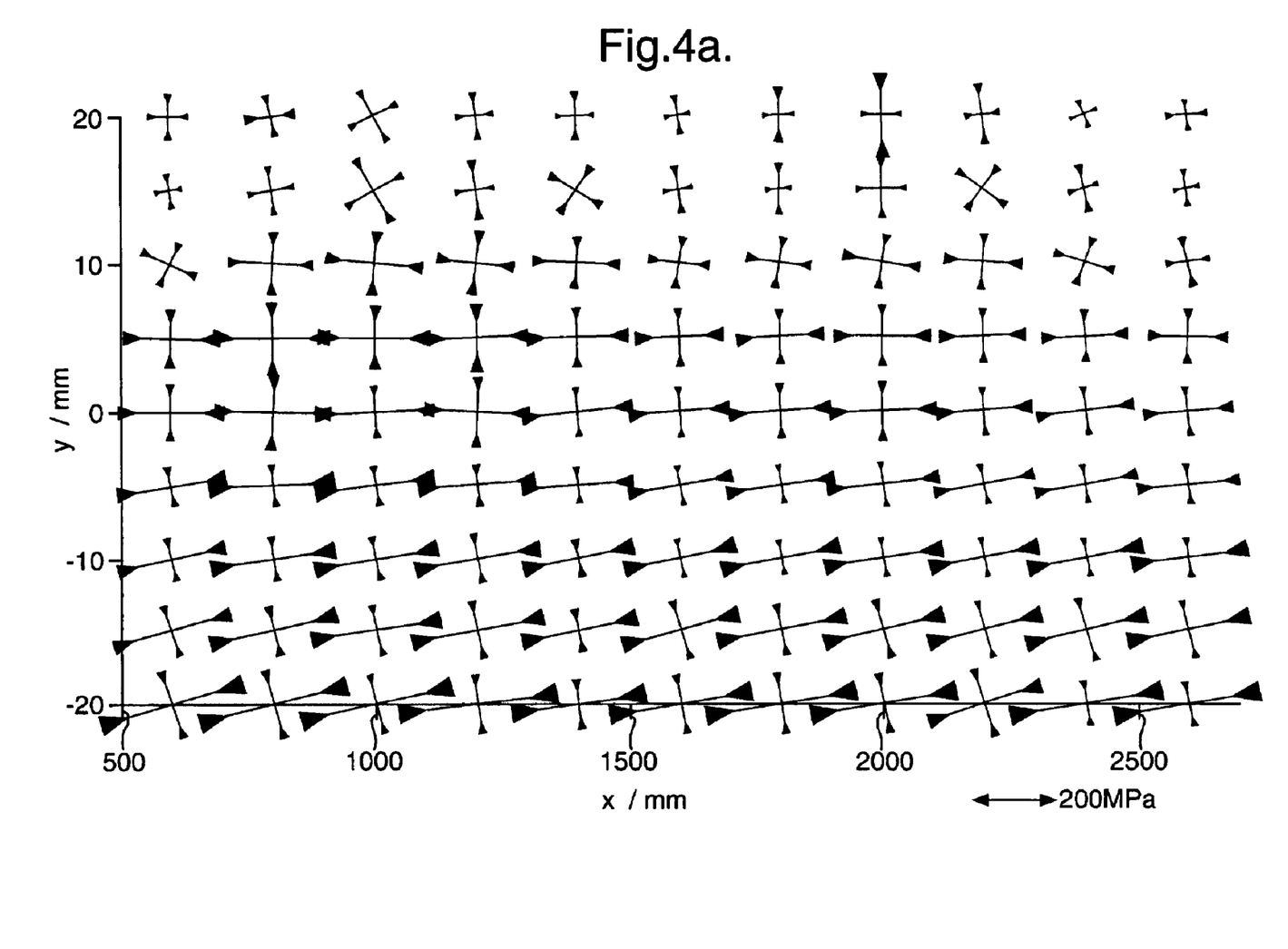
FIGS. 4a and 4b show graphically measurements of stress in sections of railhead.
Figure 4B:
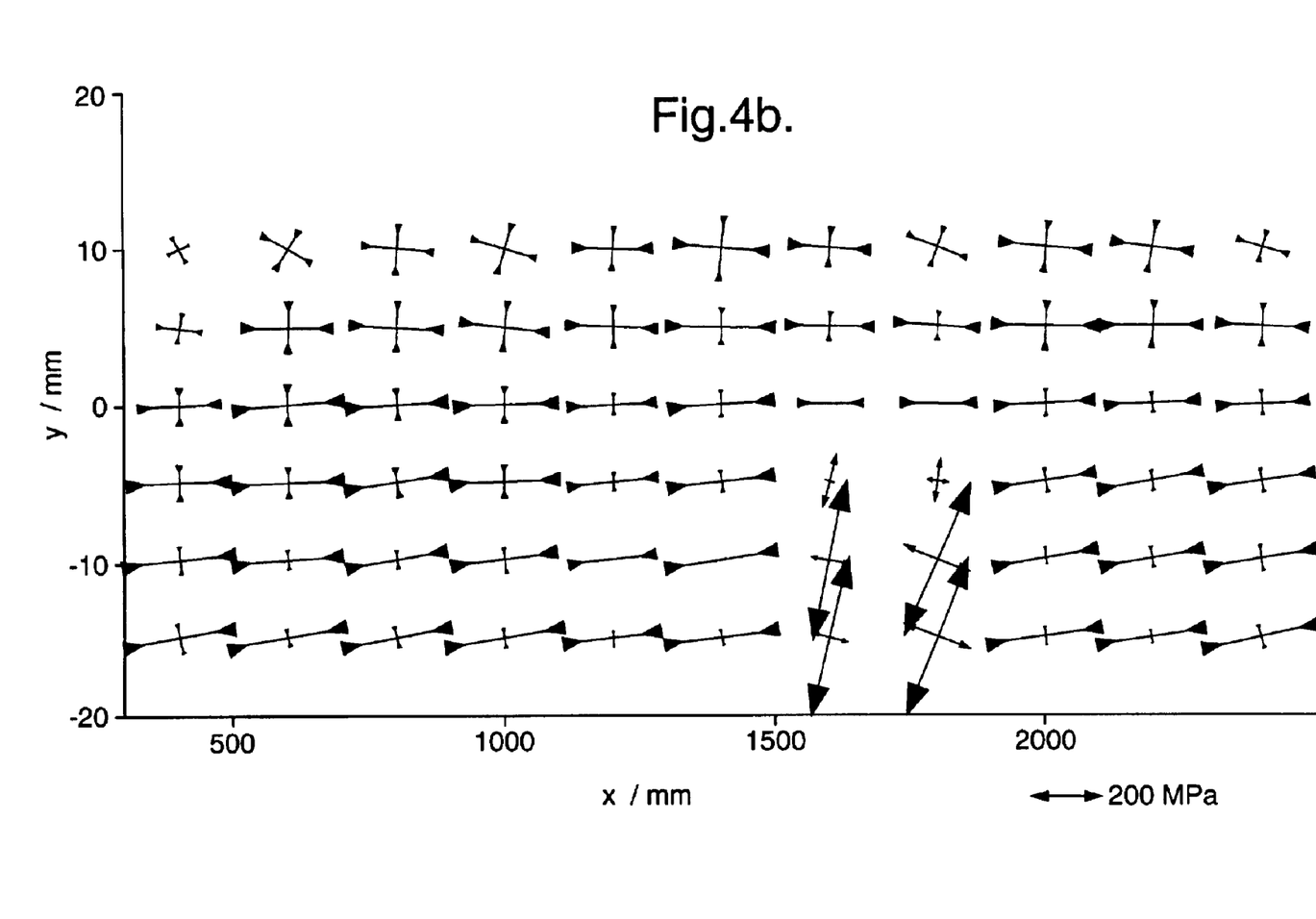

Some examples of measurements of stresses exemplifying the above changes are shown in FIG. 4, which shows graphically the magnitude and orientation of the principal stresses at a grid of positions over the surface of the rail. Measurements were made on 3 m long sections of a 16 year old rail, using a probe as described in FIGS. 1 and 2 and analysing the data as described in relation to FIG. 3. It will be appreciated that because of the varying curvature of the railhead in the transverse direction, it is essential to compensate accurately for lift-off. Measurements were made at an excitation frequency of 70 Hz so that the penetration was about 2.7 mm, and measurements were made at longitudinal intervals of 200 mm and transverse intervals of 5 mm; the probe has a spatial resolution of about 7.5 mm. The x-axis corresponds to the longitudinal axis of the railhead along its centre line, and the gauge side of the rail is in the negative y direction. The figures show the values of stress plotted as two arrows at each measurement position, their lengths representing the stress magnitudes and their directions the principal axes. The tensile and compressive stresses are represented by arrows pointing outwards or inwards respectively. FIG. 4a shows measurements on a section of rail in which no cracks have developed, whereas FIG. 4b shows measurements on a section of the same rail in which localised surface cracking has occurred.

Referring firstly to FIG. 4a it will be observed that in the portion of the railhead away from the gauge side (ie positive values of y) the stresses are typically equi-biaxial and compressive. In the region closer to the gauge side (ie negative values of y), the change of stage 1 has taken place: the generally longitudinal stress is markedly larger than the generally transverse stress, both stresses are compressive, and the orientation of the generally longitudinal principal stress axis is at about 10° to the longitudinal axis of the rail.

Referring now to FIG. 4b, in the portion of the railhead away from the gauge side the stresses are again typically equi-biaxial and compressive, at least for y=10 mm. Along the centre line of the rail, and towards the gauge side, the change of stage 2 has clearly taken place, as the generally transverse stress has become very small. In the region between about x=1500 mm and x=1800 mm (and for y<−5 mm) rolling contact fatigue has progressed through stages 3 and 4, so the orientation of the stress axes has altered, and both stresses axes are subjected to tensile residual stresses.

Figure 5:
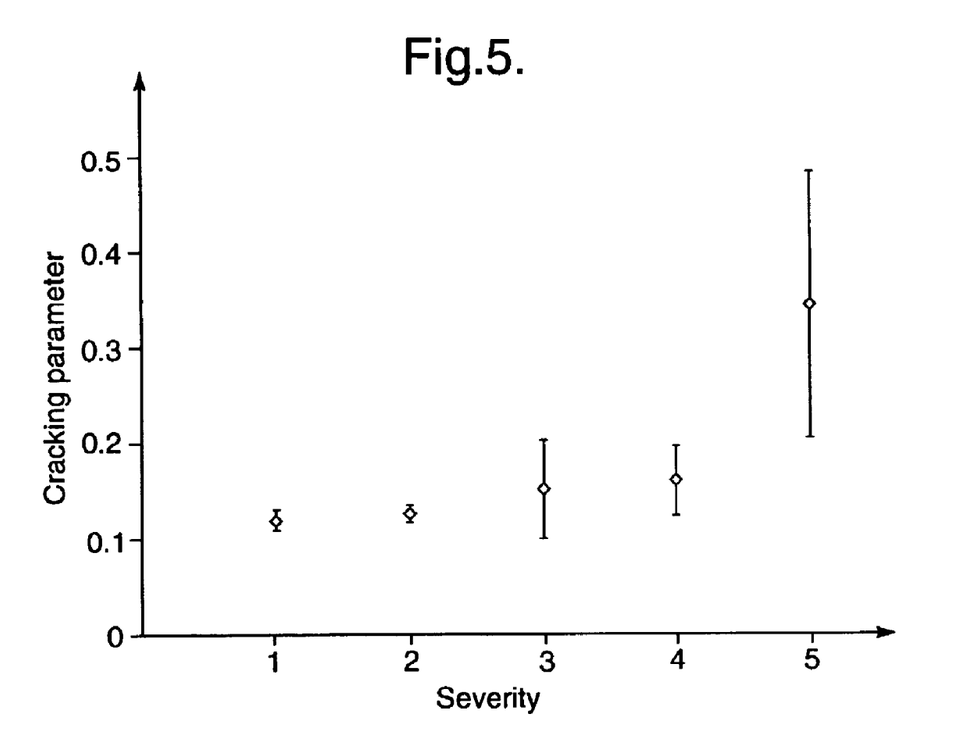
FIG. 5 shows graphically measurements of a cracking parameter.

Referring now to FIG. 5 there is shown graphically the cracking parameter derived from the leakage flux signals as described earlier for five different rails. The data is presented for the rails ranked in order of the severity of rolling contact fatigue. For each rail, measurements were made at 11 different positions for y=−10 mm, and the mean and standard deviation of these measurements are indicated. It will be appreciated that at any position of the probe 12 the flux leakage signals are indicative of any cracking in the entire area between the poles 28. It is clear that the cracking parameter correlates with the severity of cracking.

It will be appreciated that rolling contact fatigue of rails, whether manifested as head checking, tongue lipping or squats, is a major problem with railways worldwide. The particular concern is that such rail defects can lead to rail breakage unexpectedly; surface cracks tend initially to grow in a direction close to the surface, and are very difficult to see because the cracks are small and fine, but as such cracks grow a crack may develop a branch extending downward so as to break the rail. Thus by monitoring rails in situ, and measuring the stresses within the surface layer averaged over a thickness selected in the range say 0.5 mm to 4.0 mm, and detecting in particular the decrease in transverse compressive stress, the onset of rolling contact fatigue can be detected, and appropriate precautions taken. This can prevent the occurrence of rail breaks.

It will be appreciated that the measurement technique described above is particularly suited to such measurements on rails. In general one would also expect signals to be dependent upon material thickness, and electrical conductivity. However, material thickness is not relevant as long as the material is significantly thicker than the skin depth, which is always the case with rails. Furthermore the types of steel used for rails are of substantially uniform and constant electrical conductivity, so this parameter is also not relevant.

What is claimed is:

1. A method for monitoring a rail of a railway line for the development of rolling contact fatigue, the method comprising measuring the residual biaxial stresses in the surface of the rail, and monitoring changes in their magnitude or their direction, wherein the onset of rolling contact fatigue into a potentially hazardous state is indicated by the decrease of the compressive stress in the direction generally transverse to the longitudinal axis of the rail.

2. A method as claimed in claim 1 wherein the values of residual stresses in the surface are those averaged over a depth selected in the range 0.1 mm to 8.0 mm.

3. A method as claimed in claim 2 wherein the stresses are averaged over a depth in the range of 0.5 mm to 4.0 mm.

4. A method for monitoring a rail of a railway line for the development of rolling contact fatigue, the method comprising measuring the residual biaxial stresses in the surface of the rail, and monitoring changes in their magnitude or their direction, wherein the onset of rolling contact fatigue into a potentially hazardous state is indicated by a change in the orientation of the principal stress axes of about 45°.

5. A method for monitoring a rail of a railway line for the development of rolling contact fatigue, the method utilizing an electromagnetic probe that incorporates a magnetic sensor, wherein the method involves generating an alternating magnetic field in the rail, detecting the signals from the magnetic sensor with the electromagnetic probe having a multiplicity of different orientations, and hence deducing the directions of the principal stress axes in the rail, wherein the onset of rolling contact fatigue into a potentially hazardous state is indicated by a change in the orientation of the principal stress axes of about 45°.

6. A method for monitoring an object of ferromagnetic material for the development of rolling contact fatigue, the object being a rail of a railway line, the method utilizing an electromagnetic probe that incorporates a magnetic sensor, wherein the method involves generating an alternating magnetic field in the object, resolving signals from the magnetic sensor into an in-phase component and a quadrature component, mapping the in-phase and quadrature components directly into material property components and lift-off components, and deducing a value of the stress from the material property component so determined, the method comprising measuring the residual biaxial stresses in the surface of the object, monitoring changes in their magnitude or their direction, and hence detecting the onset of rolling contact fatigue into a potentially hazardous state from a detected decrease of the compressive stress in the direction generally transverse to the longitudinal axis of the rail.

7. A method as claimed in claim 6 wherein the probe also comprises a sensor for leakage flux, and the method comprises detecting from the leakage flux signals the presence of cracks.

8. A method as claimed in claim 6 wherein the values of residual stresses in the surface are those averaged over a depth selected in the range 0.1 mm to 8.0 mm.

9. A method as claimed in claim 8 wherein the stresses are averaged over a depth in the range of 0.5 mm to 4.0 mm.

10. A method as claimed in claim 6 wherein the object is of ferromagnetic material, and the method utilizes an electromagnetic probe, the method involving generating an alternating magnetic field in the object.

11. A method as claimed in claim 10 wherein the probe incorporates a magnetic sensor, and the method involves resolving signals from the magnetic sensor into an in-phase component and a quadrature component, mapping the in-phase and quadrature components directly into material property components and lift-off components, and deducing a value of the stress from the material property component so determined.

* * * * *